United States Patent
Spesard et al.

(10) Patent No.: US 9,723,836 B2
(45) Date of Patent: Aug. 8, 2017

(54) SYNERGISTIC PRE-EMERGENT AND POST-EMERGENT WEED CONTROL COMPOSITIONS AND METHODS OF USE THEREOF

(75) Inventors: Bruce Spesard, Wake Forrest, NC (US); Brian R. James, Camden, MO (US); Guillaume Huchet, Lawrence, KS (US); Raymond L. Cheek, Holt, MO (US)

(73) Assignee: BAYER CROPSCIENCE AG, Monheim am Rhein (DE)

( * ) Notice: Subject to any disclaimer, the term of this patent is extended or adjusted under 35 U.S.C. 154(b) by 812 days.

(21) Appl. No.: 12/622,082

(22) Filed: Nov. 19, 2009

(65) Prior Publication Data

US 2011/0118119 A1     May 19, 2011

(51) Int. Cl.
| | | |
|---|---|---|
| *A01N 25/00* | (2006.01) | |
| *A01N 43/80* | (2006.01) | |
| *A01N 37/38* | (2006.01) | |
| *A01N 39/02* | (2006.01) | |
| *A01N 39/04* | (2006.01) | |
| *A01N 43/68* | (2006.01) | |
| *A01N 37/40* | (2006.01) | |

(52) U.S. Cl.
CPC ............ *A01N 37/38* (2013.01); *A01N 37/40* (2013.01); *A01N 39/02* (2013.01); *A01N 39/04* (2013.01); *A01N 43/68* (2013.01); *A01N 43/80* (2013.01)

(58) Field of Classification Search
USPC ............... 504/118, 138, 140, 142, 144, 145; 514/359, 380; 549/30, 429, 492
See application file for complete search history.

(56) References Cited

U.S. PATENT DOCUMENTS

| 5,108,488 A | 4/1992 | Etheridge | |
|---|---|---|---|
| 6,455,470 B1 | 9/2002 | Parrish | |
| 6,534,444 B1 * | 3/2003 | Sievernich et al. | ............ 504/128 |
| 2006/0183637 A1 * | 8/2006 | Loughner et al. | ............ 504/101 |
| 2009/0042728 A1 * | 2/2009 | Loughner et al. | ............ 504/136 |

FOREIGN PATENT DOCUMENTS

| EP | 049071 | * | 4/1982 | ............ A01N 37/18 |
|---|---|---|---|---|
| EP | 49071 | * | 4/1982 | ............ A01N 37/18 |
| EP | 0049071 A1 | * | 4/1982 | ............ A01N 37/18 |
| EP | 223449 | * | 5/1987 | ............ A01N 43/70 |
| EP | 0223449 | * | 5/1987 | ............ A01N 43/70 |
| FR | 26525410 A1 | * | 7/1989 | |

OTHER PUBLICATIONS

International Search Report and Written Opinion for PCT/US10/55234.

* cited by examiner

*Primary Examiner* — Alton Pryor
(74) *Attorney, Agent, or Firm* — McBee Moore Woodward & Vanik IP, LLC; Susan McBee

(57) ABSTRACT

Methods and compositions for synergistic pre-emergent and post-emergent weed control are disclosed. In particular, the present disclosure relates to an herbicidal composition comprising at least one pre-emergent herbicide and at least one post-emergent herbicide, wherein the pre-emergent herbicide and the post-emergent herbicide synergistically inhibit pre-emergent and post-emergent development of a weed. The disclosure further relates to herbicidal compositions comprising isoxaben, 2,4-D, mecoprop-P, and dicamba.

9 Claims, 4 Drawing Sheets

Pre-emergent Synergy on Broadleaf Weeds

| | Weed | | DAT 7 | DAT 14 | DAT 21 | DAT 29 - 32 |
|---|---|---|---|---|---|---|
| Black medic | Medicago lupulina | O | 93 | 100 | 100 | 95 |
| | | E | 96 | 85 | 85 | 85 |
| Buckhorn plantain | Plantago lanceolata | O | 87 | 93 | 89 | 72 |
| | | E | 100 | 73 | 84 | 43 |
| White clover | Trifolium repens | O | 85 | 100 | 100 | 100 |
| | | E | 95 | 94 | 100 | 99 |
| Black medic | Medicago lupulina | O | 100 | 100 | 97 | 83 |
| Clover | Trifolium spp. | E | 100 | 100 | 100 | 91 |
| Dandelion | Taraxacum officinale | | | | | |
| Henbit | Lamium amplexicaule | | | | | |
| Pigweed | Amaranthus spp. | | | | | |
| Purslane | Portulaca spp. | | | | | |
| Red clover | Trifolium pratense | | | | | |
| Spurge | Euphorbia spp. | | | | | |

O = Observed
E = Expected

Fig. 1

Pre-emergent synergy on Broadleaf Weeds at Low-Label Rate & Sub-Label Rate

| Rate | Weed | | | 7 | 14 | 21 | DAT 29 | 42 | 56 | 91 |
|---|---|---|---|---|---|---|---|---|---|---|
| 1/2 Rate | Black medic | *Medicago lupulina* | O | | 98 | 97 | 95 | 94 | 88 | 75 |
| | | | E | | 86 | 100 | 99 | 98 | 92 | 82 |
| 1/5 Rate | Black medic | *Medicago lupulina* | O | | 92 | 85 | 73 | 53 | 48 | 35 |
| | | | E | | 94 | 98 | 98 | 99 | 98 | 94 |
| 1/2 Rate | Buckhorn plantain | *Plantago coronopus* | O | | 42 | 83 | 78 | 82 | 78 | 70 |
| | | | E | | 48 | 87 | 73 | 78 | 70 | 55 |
| 1/5 Rate | Buckhorn plantain | *Plantago coronopus* | O | | 20 | 30 | 43 | 33 | 32 | 22 |
| | | | E | | 7 | 30 | 43 | 27 | 27 | 15 |
| 1/2 Rate | White clover | *Trifolium repens* | O | | 98 | 97 | 93 | 92 | 85 | 68 |
| | | | E | | 98 | 73 | 67 | 72 | 59 | 43 |
| 1/5 Rate | White clover | *Trifolium repens* | O | | 87 | 92 | 73 | 53 | 53 | 45 |
| | | | E | | 98 | 94 | 80 | 74 | 58 | 44 |
| 1/2 Rate | Black medic Clover Purslane | *Medicago lupulina* *Trifolium spp.* *Portulaca spp.* | O | 100 | 100 | 99 | 94 | 96 | 87 | 70 |
| | | | E | 100 | 100 | 97 | 96 | 96 | 87 | 83 |
| 1/5 Rate | Black medic Clover Purslane | *Medicago lupulina* *Trifolium spp.* *Portulaca spp.* | O | 100 | 97 | 78 | 68 | 52 | 12 | 0 |
| | | | E | 100 | 100 | 85 | 70 | 52 | 12 | 0 |

O = Observed
E = Expected

Fig. 2

Post-emergent Synergy on Broadleaf Weeds at Label Rate

| Weed | | | DAT | | | | | |
|---|---|---|---|---|---|---|---|---|
| | | | 1 | 3 | 7-8 | 14-15 | 21 | 28 | 57 |
| Black medic | Medicago lupulina | O | 3 | 40 | 62 | 70 | 100 | 100 | |
| | | E | 3 | 37 | 58 | 76 | 93 | 93 | 93 |
| White clover | Trifolium repens | O | 0 | 7 | 48 | 68 | 82 | 93 | 78 |
| | | E | 0 | 2 | 33 | 66 | 83 | 93 | 77 |
| False dandelion | Pyrrhopappus carolinianus | O | 0 | 15 | 33 | 75 | | 83 | |
| Plantain | Plantago spp. | E | 0 | 17 | 35 | 57 | | 74 | |
| Rabbitfoot clover | Trifolium arvense | | | | | | | | |
| White clover | Trifolium repens | | | | | | | | |

O = Observed
E = Expected

Fig. 3

Post-emergent Synergy on Broadleaf Weeds at Low-Label Rate & Sub-Label Rate

| Rate | Weed | | 1 | 3 | 7-8 | DAT 14-15 | 21 | 28 | 61 |
|---|---|---|---|---|---|---|---|---|---|
| 1/2 Rate | White clover | O | 0 | 0 | 8 | 48 | 94 | 96 | 85 |
| | Trifolium repens | E | 0 | 0 | 17 | 83 | 99 | 98 | 85 |
| 1/5 Rate | White clover | O | 2 | 3 | 7 | 55 | 86 | 60 | 53 |
| | Trifolium repens | E | 0 | 0 | 5 | 68 | 98 | 63 | 42 |

O = Observed
E = Expected

Fig. 4

SYNERGISTIC PRE-EMERGENT AND POST-EMERGENT WEED CONTROL COMPOSITIONS AND METHODS OF USE THEREOF

Methods and compositions for synergistic pre-emergent and post-emergent weed control are disclosed.

BACKGROUND

Herbicides generally can be classified into two broad categories based on the time at which it is applied: pre-emergent herbicides and post-emergent herbicides. Pre-emergent herbicides act by preventing emergence of seedlings and therefore are useful for preventing new weed growth from developing. Post-emergent herbicides, on the other hand, are effective at eradicating fully developed weeds. Given the different mechanisms of action and the developmental stages of the weeds in which they act, one would not expect pre-emergent and post-emergent herbicides to have any effect on one another. Therefore, it was surprising to discover that certain mixtures of pre-emergent and post-emergent herbicides synergistically enhance the pre-emergent and post-emergent herbicidal effects of one another, i.e. the activities of the mixtures are greater than the sum of the individual activities. Thus, an unforeseeable synergistic effect is present, and not just an addition of activities.

SUMMARY

The present disclosure relates to herbicidal compositions comprising at least one pre-emergent herbicide and at least one post-emergent herbicide, wherein the pre-emergent herbicide and the post-emergent herbicide synergistically inhibit pre-emergent and post-emergent development of a weed. Exemplary compositions comprise at least one pre-emergent herbicide comprising at least one active ingredient selected from the group consisting of isoxaben and indaziflam; and wherein the at least one post-emergent herbicide comprises at least one active ingredient selected from the group consisting of: 2,4-D; mecoprop-P; dicamba; 2,4-DB; 2,4-DP; aminopyralid; atrazine; carfentrazone; chlorsulfuron; clopyralid; diflufenican; ethoxysulfuron; florasulam; fluoroxypyr; imazaquin; iodosulfuron; MCPA; metribuzin; metsulfuron methyl; penoxsulam; quinclorac; tembotrione; thiencarbazone methyl; and triclopyr. Such compositions further may be selected according to effectiveness at controlling a broadleaf weed selected from the group consisting of: plantain, including buckhorn plantain; clover, including white clover, red clover, and rabbitfoot clover; black medic; dandelion; henbit; pigweed; purslane; spurge; false dandelion; ground ivy; wild garlic; and wild onion.

Further disclosed are herbicidal compositions comprising isoxaben; 2,4-D; and mecoprop-P. These compositions preferably comprise from about 0.2 to about 25 W/W % of isoxaben; from about 0.05 to about 35 W/W % of 2,4-D; and from about 0.05 to about 20 W/W % of mecoprop-P. More preferably, these compositions comprise from about 2 to about 3 W/W % of isoxaben; from about 3 to about 5 W/W % of 2,4-D; and from about 0.1 to about 1 W/W % of mecoprop-P. Most preferably, these compositions comprise from about 2.4 to about 2.9 W/W % of isoxaben; from about 3.50 to about 4.32 W/W % of 2,4-D; and from about 0.7 to about 1.1 W/W % of mecoprop-P. These compositions may further comprise dicamba, preferably comprising from about 0.01 to about 25 W/W %, more preferably from about 0.1 to about 0.8 W/W %, and most preferably from about 0.4 to about 0.5 W/W % of dicamba.

Also disclosed are methods of controlling weed growth, comprising administering a composition comprising at least one pre-emergent herbicide and at least one post-emergent herbicide, wherein the pre-emergent herbicide and the post-emergent herbicide synergistically inhibit pre-emergent and post-emergent development of a weed.

BRIEF DESCRIPTION OF THE FIGURES

FIG. 1 shows data compiled from a compilation of tests for pre-emergent synergism of a composition comprising isoxaben; 2,4-D; mecoprop-P, and dicamba at full label dosage.

FIG. 2 shows data compiled from a compilation of tests for pre-emergent synergism of a composition comprising isoxaben; 2,4-D; mecoprop-P, and dicamba at one-half and one-fifth of full label dosage.

FIG. 3 shows data compiled from a compilation of tests for post-emergent synergism of a composition comprising isoxaben; 2,4-D; mecoprop-P, and dicamba at full label dosage.

FIG. 4 shows data compiled from a compilation of tests for post-emergent synergism of a composition comprising isoxaben; 2,4-D; mecoprop-P, and dicamba at one-half and one-fifth of full label dosage.

DETAILED DESCRIPTION

Traditionally, pre-emergent and post-emergent herbicides have been applied in separate formulations at different times. Because pre-emergent herbicides typically do not have any effect on weeds that have already emerged, they must be applied in early spring or late summer before weeds begin germinating and emerging. That is, while pre-emergent herbicides are effective at preventing weed growth, they typically are ineffective at killing established weeds. Likewise, post-emergent herbicides typically cannot be applied to any effect until weeds have actually emerged. That is, while post-emergent herbicides are effective at killing established weeds, they typically are ineffective at preventing weed growth.

Despite the fact that many of these pre-emergent and post-emergent herbicides have been known for some time, herbicidal compositions comprising both pre-emergent and post-emergent herbicides are quite rare. Prior to 2009, the only commercially available product was Scotts Turf Builder Max Plus 2 Weed & Feed and Crabgrass Preventer, which has limited potential for preventing emergence of broadleaf weeds.

Therefore, a need exists for effective herbicide formulations that combine pre-emergent herbicides and post-emergent herbicides, as well as methods of using such herbicidal compositions. Such compositions and methods are disclosed herein.

Further, given that pre-emergent and post-emergent herbicides act via different mechanisms and at different times in the life cycle of a weed, a person having ordinary skill in the art would not expect a pre-emergent herbicide to have any effect on a post-emergent herbicide, and vice versa. Nonetheless, it has been discovered that, in the compositions disclosed herein, the pre-emergent herbicides synergistically augment the activity of the post-emergent herbicides, and vice versa. Accordingly, compositions for controlling weed growth are disclosed, said compositions comprising at least one pre-emergent herbicide and at least one post-emergent herbicide, wherein the pre-emergent herbicide and the post-emergent herbicide synergistically inhibit pre-emergent and post-emergent development of a weed and methods of use thereof.

As used herein, "pre-emergent herbicide" refers to an herbicide that acts on newly germinating seedlings before they emerge. Exemplary pre-emergent herbicides useful in the compositions and methods disclosed herein include isoxaben and indaziflam.

Isoxaben is a benzamide compound of the HRAC Group L herbicides. It acts by inhibiting cellulose synthesis, thereby inhibiting cell wall formation and blocking emergence of seedlings. Isoxaben controls the broadest spectrum of broadleaf weeds of commonly-used pre-emergent herbicides; can be used on all major turf types, including cool season (C3) turf types, e.g. Kentucky bluegrass, fescue, and ryegrass; lasts for up to six months after application; and does not stain exterior hardscapes.

Indaziflam belongs to the chemical class of alkylazines. It inhibits cell wall biosynthesis and acts on meristematic cell growth, thereby effectively controlling a broad spectrum of weeds, including species which are difficult to eliminate such as annual bluegrass, goosegrass, ryegrass and goosefoot. Indaziflam is an excellent mixing partner and can be used either pre- or post-emergent in conjunction with post-emergent herbicides. Another advantage of indaziflam is the low application rate. Because of the long-lasting action and the broad spectrum of activity, the number of applications can be reduced. Indaziflam is particularly useful for warm season (C4) turf types, such as bermudagrass, zoysia, St. Augustinegrass, and centipedegrass.

These compounds are effective at preventing emergence of a number of weeds, including but not limited to the following broadleaf weeds: plantain, including buckhorn plantain; clover, including white clover, red clover, and rabbitfoot clover; black medic; dandelion; henbit; pigweed; purslane; spurge; false dandelion; ground ivy; wild garlic; and wild onion.

As used herein, "post-emergent herbicides" refers to herbicides that are active only on emerged plants. Exemplary pre-emergent herbicides useful in the compositions and methods disclosed herein include 2,4-D; mecoprop-P; dicamba; 2,4-DB; 2,4-DP; aminopyralid; atrazine; carfentrazone; chlorsulfuron; clopyralid; diflufenican; ethoxysulfuron; florasulam; fluoroxypyr; imazaquin; iodosulfuron; MCPA; metribuzin; metsulfuron methyl; penoxsulam; quinclorac; tembotrione; thiencarbazone methyl; and triclopyr.

2,4-D is a synthetic auxin, which is a class of plant growth regulators. It is absorbed through the leaves and is translocated to the meristems of the plant. Uncontrolled, unsustainable growth ensues, causing stem curl-over, leaf withering, and eventual plant death.

mecoprop-P is a selective, hormone-type phenoxy herbicide. It is used on ornamentals and sports turf, for forest site preparation, and on drainage ditch banks for selective control of surface creeping broadleaf weeds such as clovers, chickweed, lambsquarters, ivy, plantain and others. It is also used on wheat, barley, and oats. Mecoprop is absorbed by plant leaves and translocated to the roots. It affects enzyme activity and plant growth. It acts relatively slowly requiring three to four weeks for control Dicamba is an auxin analog, causing uncontrollable growth eventually leading to plant death.

2,4-D, mecoprop-P, and dicamba frequently are used in combination with one another, both in two-way and three-way post-emergent herbicides. For example, one commercially-available two-way herbicide is Scotts Turfbuilder Plus 2 Weed Control, which comprises 2,4-D and mecoprop-P. Exemplary three-way post-emergent herbicides include Bayer Advanced Southern Weed Killer for Lawns and PBI/Gordon's Trimec Growth Regulator Herbicide, both of which comprise 2,4-D, mecoprop-P, and dicamba.

These post-emergent compounds, as well as the two-way and three-way post-emergent formulations set forth above, are effective at killing a number of established weeds, including but not limited to the following broadleaf weeds: plantain, including buckhorn plantain; clover, including white clover, red clover, and rabbitfoot clover; black medic; dandelion; henbit; pigweed; purslane; spurge; false dandelion; ground ivy; wild garlic; and wild onion.

Preferred compositions comprise isoxaben; 2,4-D; and mecoprop-P. These compositions preferably comprise from about 0.2 to about 25 W/W % of isoxaben; from about 0.05 to about 35 W/W % of 2,4-D; and from about 0.05 to about 20 W/W % of mecoprop-P. More preferably, these compositions comprise from about 2 to about 3 W/W % of isoxaben; from about 3 to about 5 W/W % of 2,4-D; and from about 0.1 to about 1 W/W % of mecoprop-P. Most preferably, these compositions comprise from about 2.4 to about 2.9 W/W % of isoxaben; from about 3.50 to about 4.32 W/W % of 2,4-D; and from about 0.7 to about 1.1 W/W % of mecoprop-P.

More preferable compositions comprise isoxaben; 2,4-D; mecoprop-P, and dicamba. These compositions preferably comprise from about 0.2 to about 25 W/W % of isoxaben; from about 0.05 to about 35 W/W % of 2,4-D; from about 0.05 to about 20 W/W % of mecoprop-P, and from about 0.01 to about 25 W/W % dicamba. More preferably, these compositions comprise from about 2 to about 3 W/W % of isoxaben; from about 3 to about 5 W/W % of 2,4-D; from about 0.1 to about 1 W/W % of mecoprop-P; and from about 0.1 to about 0.8 W/W % of dicamba. Most preferably, these compositions comprise from about 2.4 to about 2.9 W/W % of isoxaben; from about 3.50 to about 4.32 W/W % of 2,4-D; from about 0.7 to about 1.1 W/W % of mecoprop-P; and from about 0.4 to about 0.5 W/W % of dicamba.

The presently disclosed compositions can be present both as mixed formulations of the components, if appropriate with other active compounds, additives and/or customary formulation auxiliaries, which are then applied in a customary manner diluted with water, or be prepared as so-called tank mixes by joint dilution of the separately formulated or partially separately formulated components with water.

The compositions disclosed herein can be formulated in various ways depending on the prevailing biological and/or chemico-physical parameters. Examples of suitable formulation options are: wettable powders (WP), emulsifiable concentrates (EC), aqueous solutions (SL), emulsions (EW), such as oil-in-water and water-in-oil emulsions, sprayable solutions or emulsions, oil- or water-based dispersions, suspoemulsions, dusts (DP), seed-dressing compositions, granules for broadcasting and soil application, or water-dispersible granules (WG)1 ULV formulations, microcapsules or waxes.

Based on these formulations it is also possible to produce combinations with other pesticidally active substances, such as other herbicides, fungicides or insecticides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic or nonionic type (wetting agents, dispersants), for example polyethoxylated alkyl phenols, polyethoxylated fatty alcohols, polyethoxylated fatty amines, alkanesulfonates, alkylbenzenesulfonates, sodium ligninsulfonate, sodium 2,2'-dinaphthylmethane-6,61-disulfonate, sodium dibutylnaphthalene-sulfonate or else sodium oleoyl-methyltaurinate.

Emulsifiable concentrates are prepared by dissolving the active compound in an organic solvent, for example butanol, cyclohexanone, dimethylformamide, xylene or else relatively high-boiling aromatic compounds or hydrocarbons with the addition of one or more surfactants of ionic or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters or polyoxyethylene sorbitan esters.

Dusts are obtained by grinding the active compound with finely divided solid substances, for example talc, natural clays, such as kaolin, bentonite and pyrophyllite, or diatomaceous earth.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by processes such as spray-drying, fluidized-bed granulation, disk granulation, mixing using high-speed mixers, and extrusion without solid inert material.

The agrochemical formulations generally contain from 0.1 to 99% by weight, in particular from 2 to 95% by weight, of active compounds, the following concentrations being customary, depending on the type of formulations: In wettable powders the concentration of active compound is, for example, from about 10 to 95% by weight, the remainder to 100% by weight consisting of customary formulation constituents. In emulsifiable concentrates the concentration of active compound can be, for example, from 5 to 80% by weight. Formulations in the form of dusts usually contain from 5 to 20% by weight of active compound, while sprayable solutions contain from about 0.2 to 25% by weight of active compound. In the case of granules, such as dispersible granules, the content of active compound depends partly on whether the active compound is in liquid or solid form and on which granulation auxiliaries and fillers that are used. In water-dispersible granules the content is generally between 10 and 90% by weight.

In addition, said formulations of active compound may comprise the tackifiers, wetting agents, dispersants, emulsifiers, preservatives, antifreeze agents and solvents, fillers, colorants and carriers, antifoams, evaporation inhibitors, pH and viscosity regulators, thickeners and/or fertilizers which are customary in each case.

For use, the formulations, which are in commercially available form, are, if appropriate, diluted in a customary manner, for example using water in the case of wettable powders, emulsifiable concentrates, dispersions and water-dispersible granules. Preparations in the form of dusts, soil granules, granules for spreading and sprayable solutions are conventionally not diluted any further with other inert substances prior to use.

EXAMPLES

Example 1

Formulation of the Four-Way Isoxaben-2,4-D-Mecoprop-P-Dicamba Herbicide. Isoxaben is a water insoluble compound, while 2,4-D, mecoprop-P, and dicamba all are water soluble. Incorporating water-insoluble active ingredients with water soluble inactive ingredients can be problematic. To address this, a fine particulate suspension of isoxaben was created in an aqueous solution by using a polymeric suspension aide. Briefly, mecoprop-P and dicamba were converted to potassium salts, then added to an aqueous solution along with a 2,4-D DMA salt. Isoxaben was wet milled to obtain fine-milled insoluble isoxaben particulates, although other methods of milling can be used interchangeably, for example, dry milling and air milling. The isoxaben particulates were then physically stabilized by adding a polymeric suspension aide and adjusting the pH of the solution. Polymeric suspension aides and methods of use are well known in the art. Further, other thickening agents are well known in the art and can be used to the same effect.

Example 2

Calculation of Pre-Emergent Synergism at Full Label Rate.

As a first test, a four-way aqueous suspension comprising isoxaben; 2,4-D; mecoprop-P, and dicamba was made according to Example 1 at the concentrations set forth in Table 1 and tested for pre-emergent synergism.

TABLE 1

| No. | Description | AI Conc. | Dosage | Dosage Unit | Transformed Dosage | Transformed Dosage Unit |
|---|---|---|---|---|---|---|
| 1 | UNTREATED UNTREATED | | | | | |
| 2 | Isoxaben Only | 2.65 | 549.6 | G A/HA | 6.4 | OZ/1000 FT2 |
|   | ISOXABEN | 2.65 | 549.6 | | | |
| 3 | No Isoxaben | 6.11 | 1301 | G A/HA | 6.4 | OZ/1000 FT2 |
|   | 2,4-D AS SALT | 4.73 | 1007 | | | |
|   | MECOPROP-P | 0.94 | 200.2 | | | |
|   | DICAMBA | .44 | 93.7 | | | |
| 4 | 4-Way pre/post composition | 7.97 | 1700 | G A/HA | 6.4 | OZ/1000 FT2 |
|   | ISOXABEN | 2.65 | 565 | | | |
|   | 2,4-D | 3.94 | 840 | | | |
|   | MECOPROP-P | .94 | 200.5 | | | |
|   | DICAMBA | .44 | 93.85 | | | |

To test for synergism, broadleaf weed seeds were planted in three replicates of 10 m² plots for each of four conditions: (1) untreated; (2) containing isoxaben only; (3) containing post-emergent herbicides only; and (4) containing a four-way pre/post composition. The plots were then treated with the respective solutions at the rate set forth in Table 1 immediately upon planting and three additional times afterward. Plots were then rated for percent suppression as compared to control. Expected control was approximated by using Gowing's calculation:

$$E=X+Y-XY/100,$$

where

E=Expected % Control of Herbicides A+B,
X=Observed % Control of Herbicide A, and
Y=Observed % Control of Herbicide B.
The data was then analyzed as follows:

| | |
|---|---|
| Synergism: | Observed control > Expected control |
| Neutral: | Observed control = Expected control |
| Antagonism: | Observed control < Expected control |

As can be seen at FIG. 1, synergism was observed for the 4-way pre/post formulation for black medic alone; buckhorn plantain alone; white clover alone; and the mix of black medic, clover, dandelion, henbit, pigweed, purslane, red clover, and spurge.

Example 3

Calculation of Pre-Emergent Synergism at One-Half and One-Fifth Full Label Rate.

Example 2 was repeated using the same compositions, only at doses of one-half and one fifth of the transformed dosage set forth in Table 1. As can be see in FIG. 2, synergism was observed at the one-half transformed dosage for all of the weed mixes tested. Synergism also was observed at the one-fifth transformed dosage for buckhorn plantain and white clover.

Example 4

Calculation of Post-Emergent Synergism at Full Label Rate.

A four-way aqueous suspension comprising isoxaben; 2,4-D; mecoprop-P, and dicamba was made according to Example 1 at the concentrations set forth in Table 1. A test field was then subdivided into three replicates of 10 m² plots for each of four conditions: (1) untreated; (2) containing isoxaben only; (3) containing post-emergent herbicides only; and (4) containing a four-way pre/post composition. Broadleaf weeds were identified and tallied in each plot. The plots were then treated with the respective solutions at the rate set forth in Table 1. Three additional treatments were made thereafter. Data were taken at 1, 3, and 7 days and 2, 3, 4, and 8 weeks after the initial application and analyzed as in Example 2. As can be seen at FIG. 3, synergism was observed for black medic; white clover; and a mix of false dandelion, plantain, rabbitfoot clover, and white clover.

Example 5

Calculation of Post-Emergent Synergism at One-Half and One-Fifth Full Label Rate.

Example 4 was repeated using the same compositions, only at doses of one-half and one fifth of the transformed dosage set forth in Table 1. As can be see in FIG. 4, synergism was observed at the one-fifth rate for white clover.

What is claimed is:

1. A herbicidal composition, comprising at least one pre-emergent herbicide and at least two post-emergent herbicides, wherein the herbicidal composition comprises amounts of the pre-emergent herbicide and the post-emergent herbicides effective to inhibit both (i) pre-emergent and (ii) post-emergent development of a weed, wherein the at least one pre-emergent herbicide comprises the active ingredient isoxaben, and wherein the at least two post-emergent herbicides comprise 2,4-D and mecoprop-P, wherein the composition further comprises dicamba, and wherein the herbicides in the composition consisting of isoxaben, 2,4-D, mecoprop-P and dicamba, wherein the composition comprises from about 0.2 to about 25 W/W % of the isoxaben; from about 0.05 to about 35 W/W % of the 2,4-D; from about 0.05 to about 20 W/W % of the mecoprop-P; and from about 0.01 to about 25 W/W % of the dicamba.

2. The herbicidal composition of claim 1 comprising:
from about 2 to about 3 W/W % of the isoxaben;
from about 3 to about 5 W/W % of the 2,4-D; and
from about 0.1 to about 1 W/W % of the mecoprop-P.

3. The herbicidal composition of claim 1 comprising:
from about 2.4 to 2.9 W/W % of the isoxaben;
from about 3.50 to about 4.32 W/W % of the 2,4-D; and
from about 0.7 to about 1.1 W/W % of the mecoprop-P.

4. The herbicidal composition of claim 2 comprising from about 0.1 to about 0.8 W/W % of the dicamba.

5. The herbicidal composition of claim 3 further comprising from about 0.4 to about 0.5 W/W % of dicamba.

6. A method of controlling weed growth, said method comprising applying a composition comprising at least one pre-emergent herbicide and at least two post-emergent herbicides to a weed or seed thereof or to a field where the weeds are expected to grow, wherein the composition comprises amounts of the pre-emergent herbicide and the post-emergent herbicides effective to inhibit both (i) pre-emergent and (ii) post-emergent development of a weed, wherein the at least one pre-emergent herbicide comprises the active ingredient isoxaben, and wherein the at least two post-emergent herbicides comprise 2,4-D and mecoprop P, wherein the composition further comprises dicamba, and wherein the herbicides in the composition consisting of isoxaben, 2,4-D, mecoprop-P and dicamba, wherein the composition comprises from about 0.2 to about 25 W/W % of the isoxaben; from about 0.05 to about 35 W/W % of the 2,4-D; from about 0.05 to about 20 W/W % of the mecoprop-P; and from about 0.01 to about 25 W/W % of the dicamba.

7. The method of claim 6 wherein the weed is selected from the group consisting of: plantain, including buckhorn plantain; clover, including white clover, red clover, and rabbitfoot clover; black medic; dandelion; henbit; pigweed; purslane; spurge; false dandelion; ground ivy; wild garlic; wild onion; and wild violet.

8. The method of claim 6, comprising:
from about 2 to about 3 W/W % of the isoxaben;
from about 3 to about 5 W/W % of the 2,4-D; and
from about 0.1 to about 1 W/W % of the mecoprop-P.

9. The method of claim 6, comprising: from about 2.4 to 2.9 W/W % of the isoxaben;
from about 3.50 to about 4.32 W/W % of the 2,4-D; and
from about 0.7 to about 1.1 W/W % of the mecoprop-P.

* * * * *